United States Patent [19]

Yoshino et al.

[11] Patent Number: 4,632,528
[45] Date of Patent: Dec. 30, 1986

[54] METHOD FOR DETERMINING REFRACTIVE INDEX OF AN OBJECT

[75] Inventors: Hisakazu Yoshino; Kazutoshi Takagi; Yoshitaka Torii, all of Tokyo, Japan

[73] Assignee: Tokyo Kogaku Kikai Kabushiki Kaisha, Tokyo, Japan

[21] Appl. No.: 722,991

[22] Filed: Apr. 15, 1985

Related U.S. Application Data

[63] Continuation of Ser. No. 412,176, Aug. 27, 1982, abandoned.

[30] Foreign Application Priority Data

Aug. 31, 1981 [JP] Japan ................. 56-136595

[51] Int. Cl.⁴ .................. A61B 3/10; G01N 21/41
[52] U.S. Cl. .................... 351/211; 351/212; 356/128; 356/382
[58] Field of Search .................. 351/211, 212, 214; 356/128, 382

[56] References Cited

U.S. PATENT DOCUMENTS

4,019,813 4/1977 Cornsweet et al. ............... 351/212
4,176,937 12/1979 Kawase .

OTHER PUBLICATIONS

D. M. Maurice and A. A. Giardini, "A Simple Optical Apparatus for Measuring the Corneal Thickness, and the Average Thickness of the Human Cornea" British Journal of Ophthalmology, vol. 35, pp. 169-177.

Primary Examiner—John K. Corbin
Assistant Examiner—P. Dzierzynski
Attorney, Agent, or Firm—Brumbaugh, Graves, Donohue & Raymond

[57] ABSTRACT

Method for determining a refractive index of an object in which the object is illuminated with a slit pattern of illumination light to form an optical section of the section of the object and the optical section is observed in two directions to determine apparent thickness of the optical section in these directions. Operations are carried out to obtain the refractive index of the object from the apparent thickness of the optical section.

4 Claims, 7 Drawing Figures

METHOD FOR DETERMINING REFRACTIVE INDEX OF AN OBJECT

This application is a continuation of application Ser No. 412,176, filed on Aug. 27, 1982 now abandoned.

BACKGROUND OF THE INVENTION

This invention relates to a method of determining the refractive index of an object, particularly a method of determining the refractive index of the cornea of a human eye.

SUMMARY OF THE INVENTION

Regarding the refractive index of the cornea of human eye, various investigations have been made by many researchers. For instance, Gullstrand determined it to be 1.376 while Lohnstein gave it as 1.3739. Kraus announced it 1.3507 and Chossat figured it to be 1.33 while Maurice put the figure at 1.375.

However, all of these values of the corneal refractive index are those determined from the dry cornea extirpated from the human body or those calculated from the refractive indices and volumes of collugen and inter-fiber substances.

For determination of the refractive index of the cornea in vivo such as the cornea of a living human eye, there are known methods in which the refractive index of the cornea is determined by using Pulfrich's refractometer or Abbe's refractometer immediately after extirpation of the cornea before it has time to dry out or suffer other denaturing. In the determination by use of said refractometers, it is necessary to conduct the determination with the medium of a liquid, such as monobromonaphthalene, having a higher refractive index than the object specimen (cornea). In these methods, however, since the cornea inevitably undergoes denaturing due to said intermediate liquid, the determined refractive index differs from that of the cornea in vivo. It was thus quite impossible with these methods to determine the refractive index of the cornea of a living eye as it is necessary therefor to extirpate the cornea from a living human eye.

The present invention has been made with a view to eliminating these disadvantages of the conventional methods.

An object of this invention, therefore, is to provide a novel method for determining the refractive index of an object.

Another object of this invention is to provide a method which is capable of directly determining the refractive index of the cornea of a living eye without extirpating the cornea of the living eye and also without intermediation of any chemical agent.

Still another object of this invention is to provide an apparatus for carrying out the aforementioned method of the invention.

According to the present invention, the above and other objects can be accomplished by a method for determining a refractive index of an object which comprises steps of illuminating the object in one direction with a slit pattern of light to form an optical section in said object, determining apparent thicknesses of the section in said object in at least two directions relative to the direction of illumination of said slit pattern of illumination light, and calculating the refractive index of said object from the thus determined at least two apparent thicknesses.

The object of which refractive index is to be determined may be a transparent body which can not be subjected to determination by a conventional refractometer in a partially cut out from, of which contact with the refractometer is undesirable, and which are liable to suffer denaturing under the action of the intervening medium. As typical examples of such object, there may be cited cornea of a living eye, crystalline lens and the like, but in the following descriptions of the invention, only the case of application of the invention to the cornea is described for the convenience of explanation.

According to a further aspect of the present invention, there is provided a method for determining a refractive index of an object which comprises steps of illuminating the object in at least two directions with slit patterns of light to form at least two optical sections in said object, observing said at least two optical sections in one direction to determine apparent thicknesses of said optical sections, and calculating the refractive index of said object from the thus determined apparent thicknesses.

The method of this invention can be practiced by using an apparatus which is also provided according to this invention and which comprises an illuminating system for applying a slit pattern of light to and thereby illuminating the cornea of an eye to be examined to produce an image of or section of the cornea, a measuring optical system for measuring apparent thicknesses of the cornea from the image of the section of the cornea formed by said illumination system, means for determining the apparent thicknesses of said image of the cornea formed by said optical system, and operation means for calculating the refractive index of the cornea from the apparent thicknesses determined by said determining means.

Thus, the present invention provides a method for quickly, simply and accurately determining the refractive index of the cornea in a living body and an apparatus for conducting the determination without extirpating the cornea from the eye and also without causing any pain to the subject being examined since no part of the apparatus physically contacts the eye, and also because neither the method nor the apparatus require any intermediary substance such as a chemical agent.

The above and other objects and features of the present invention will become apparent from the following descriptions of preferred embodiments taking reference to the accompanying drawings, in which.

A principle of this invention is to determine two apparent thicknesses of the cornea as observed along two different directions with respect to the optical axis of the cornea, to thereby calculate the refractive index of the cornea based on these determined apparent thicknesses.

Figure 1:
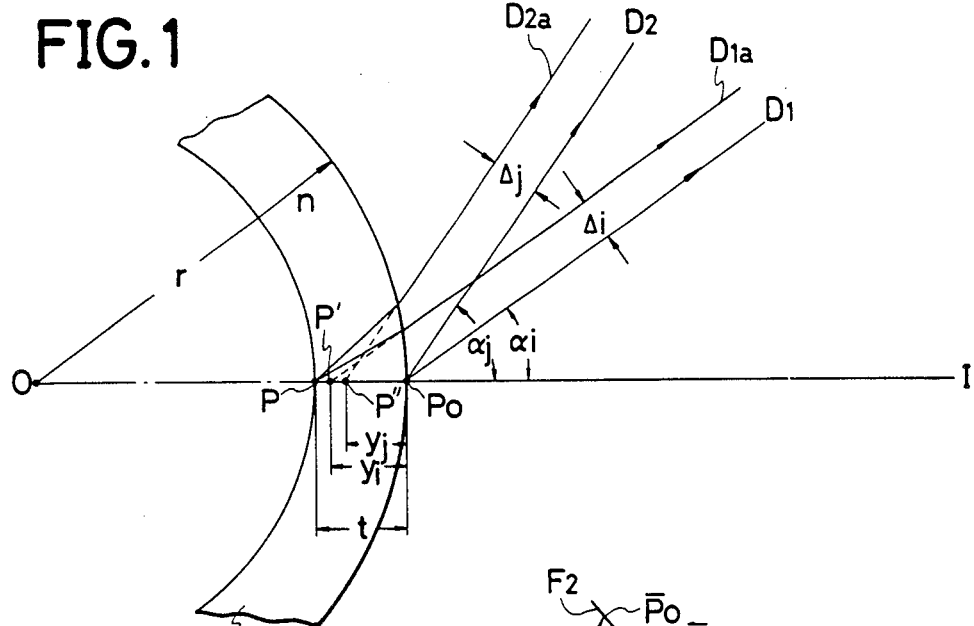
FIG. 1 is a diagrammatic illustration showing the principle of this invention.

Referring now to the drawings, particularly to FIG. 1, there is shown the principle of this invention. In FIG. 1, it will be noted that a slit pattern of light I is directed on the cornea C of an eye in the direction of the center of curvature of the front side of the cornea. The light is then scattered in the cornea in various directions. Consideration will now be made on two light fluxes $D_1$ and $D_2$ among the scattered light fluxes. With respect to the light flux $D_1$ which is directed at an angle of $\alpha_i$ with the incident light I, the light beam $D_{1a}$ from the point P of intersection of the incident light I with the rear side of the cornea is observed as if it were emitted from the point P', and hence in measurement of the thickness t of the cornea, there is actually given the apparent thickness $Y_i$. In the case of the light flux $D_2$ which is directed at an angle of $\alpha_j$ with the incident light I, the light beam $D_{2a}$ projected from the point P is observed as if it were emitted from the point P'', and hence the measurement of the thickness of the cornea with this light flux gives an apparent thickness $Y_j$. Here, assume the following formulae applies:

$$M_i = \sin\alpha_i \left(1 - \frac{y_i}{r}\right) \quad (1)$$

$$M_j = \sin\alpha_j \left(1 - \frac{Y_j}{r}\right)$$

(wherein r is the radius of curvature of the front side of the cornea)

$$N_i = \alpha_i - \sin^{-1} M_i \quad (2)$$
$$N_j = \alpha_j - \sin^{-1} M_j$$

and also give the following formulae:

$$a = \left\{\left(\frac{\sin N_i}{M_i}\right)^2 - \left(\frac{\sin N_j}{M_j}\right)^2\right\}^2 \quad (3)$$

$$b = \sin^2 N_i \sin^2 N_j \left(\frac{1}{M_i^2} + \frac{1}{M_j^2}\right) +$$

$$\left(\frac{\sin^2 N_i}{M_i^2} + \frac{\sin^2 N_j}{M_j^2}\right) \times [\cos N_i \cos N_j - 1]$$

$$c = [\cos N_i - \cos N_j]^2$$

Then the refractive index n of the cornea C is given by:

$$n = \sqrt{2\left(\frac{\sqrt{b^2 - ac} - b}{a}\right)} \quad (4)$$

Figure 2:
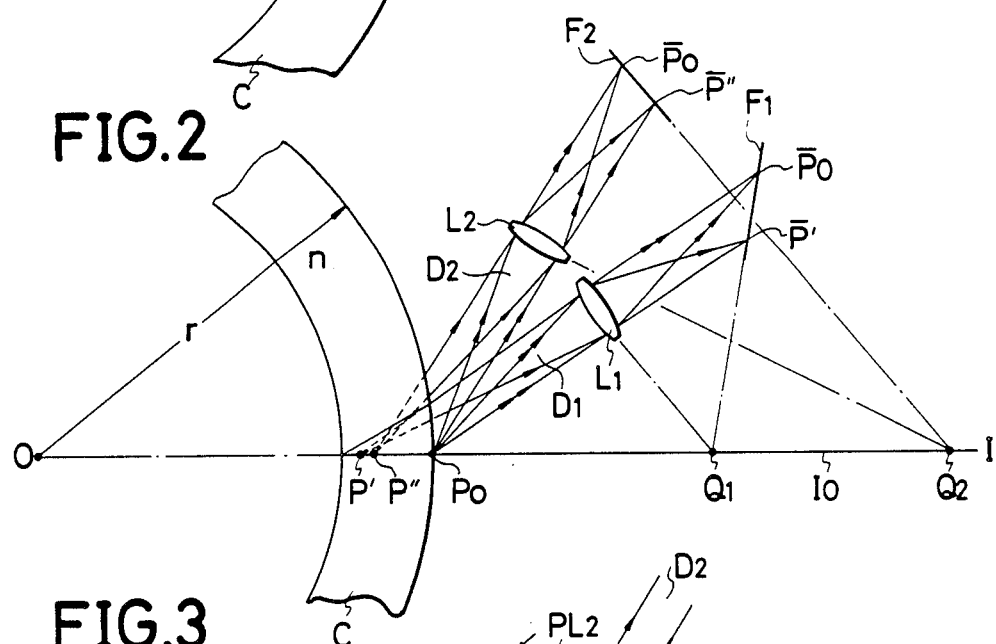
FIG. 2 is a diagrammatic illustration showing the principle in a first embodiment of this invention.

In one method of determining the apparent thicknesses $y_i$ and $y_j$, the light fluxes $D_1$, $D_2$ from the cornea are focussed to form images of the cornea according to the Scheimpflug's principle. Referring to FIG. 2, the light beams in the light flux $D_1$ from the scattering points $P_0$, P' on the section of the cornea in the plane of the slitted light I are focussed through a lens $L_1$ which is disposed in a plane intersecting the optical axis $I_0$ of the light I at the point $Q_1$ so as to form respective images on a plane $F_1$ which is intersecting the optical axis $I_0$ also at the point $Q_1$. Since the image $\overline{P_0}$ of the scattering point $P_0$ and the image $\overline{P'}$ of the scattering point P' are sharply formed on the plane $F_1$, it is possible to determine the apparent thickness $y_i$ between the two points $P_0$ and P' from the image points $\overline{P_0}$ and $\overline{P'}$ on the plane $F_1$. Likewise, the scattered light beams in the light flux $D_2$ from the scattering points $P_0$ and P'' are passed through a lens $L_2$ disposed in a plane intersecting the optical axis $I_0$ of the light I at the point $Q_2$ so as to form corresponding images on a plate $F_2$ so disposed that it intersects the optical axis $I_0$ also at the point $Q_2$. Thus, the apparent thickness $y_j$ can be determined from the image points $\overline{P_0}$ and $\overline{P''}$ on the plane $F_2$.

Figure 3:
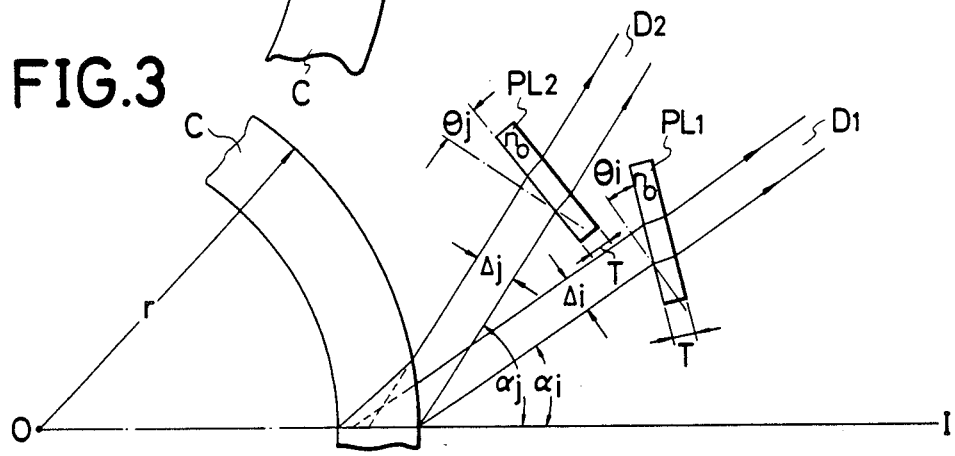
FIG. 3 is a diagrammatic illustration showing the principle in a second embodiment of this invention.

In another method of determining the apparent thicknesses $y_i$, $y_j$, plane-parallel optical elements $PL_1$, $PL_2$ are disposed on the path of the light beams in the light fluxes $D_1$, $D_2$ as shown in FIG. 3. The apparent thicknesses are then determined from angles of rotation $\theta_i$, $\theta_j$ of the plane-parallel elements $PL_1$, $PL_2$. According to this method, if the scattering angles $\alpha_i$ and $\alpha_j$ are known, the apparent thicknesses $y_i$, $y_j$ can be obtained by determining the apparent widths $\Delta_i$, $\Delta_j$ of the light fluxes from the following formulae:

$$\left.\begin{array}{l}\Delta_i = y_i \sin\alpha_i \\ \Delta_j = y_j \sin\alpha_j\end{array}\right\} \quad (5)$$

The apparent widths $\Delta_i$, $\Delta_j$ can be determined from the following formulae:

$$\Delta_i = \frac{T}{\cos\left[\sin^{-1}\left(\frac{\sin\theta_i}{n_o}\right)\right]} \sin\left[\theta_i - \sin^{-1}\left(\frac{\sin\theta_i}{n_o}\right)\right] \quad (6)$$

$$\Delta_j = \frac{T}{\cos\left[\sin^{-1}\left(\frac{\sin\theta_j}{n_o}\right)\right]} \sin\left[\theta_j - \sin^{-1}\left(\frac{\sin\theta_j}{n_o}\right)\right]$$

wherein

T: thickness of the plane-parallel elements $PL_1$, $PL_2$.
$n_o$: refractive index of the plane-parallel elements.
$\theta_i$, $\theta_j$: angles of rotation.

Hence, from the formulae (5), the apparent thicknesses $y_i$, $y_j$ are given by:

$$\left.\begin{array}{l}y_i = \frac{\Delta_1}{\sin\alpha_i} \\ y_j = \frac{\Delta_1}{\sin\alpha_j}\end{array}\right\} \quad (7)$$

Thus, the apparent thicknesses $y_i$, $y_j$ can be determined according to either of the above two methods, and after introducing them into the formula (1), the refractive index of the cornea can be determined from the formulae (2), (3) and (4).

The invention is described in further detail hereinbelow by way of embodiments thereof, which should not be taken as limiting the scope of the invention.

Figure 4:
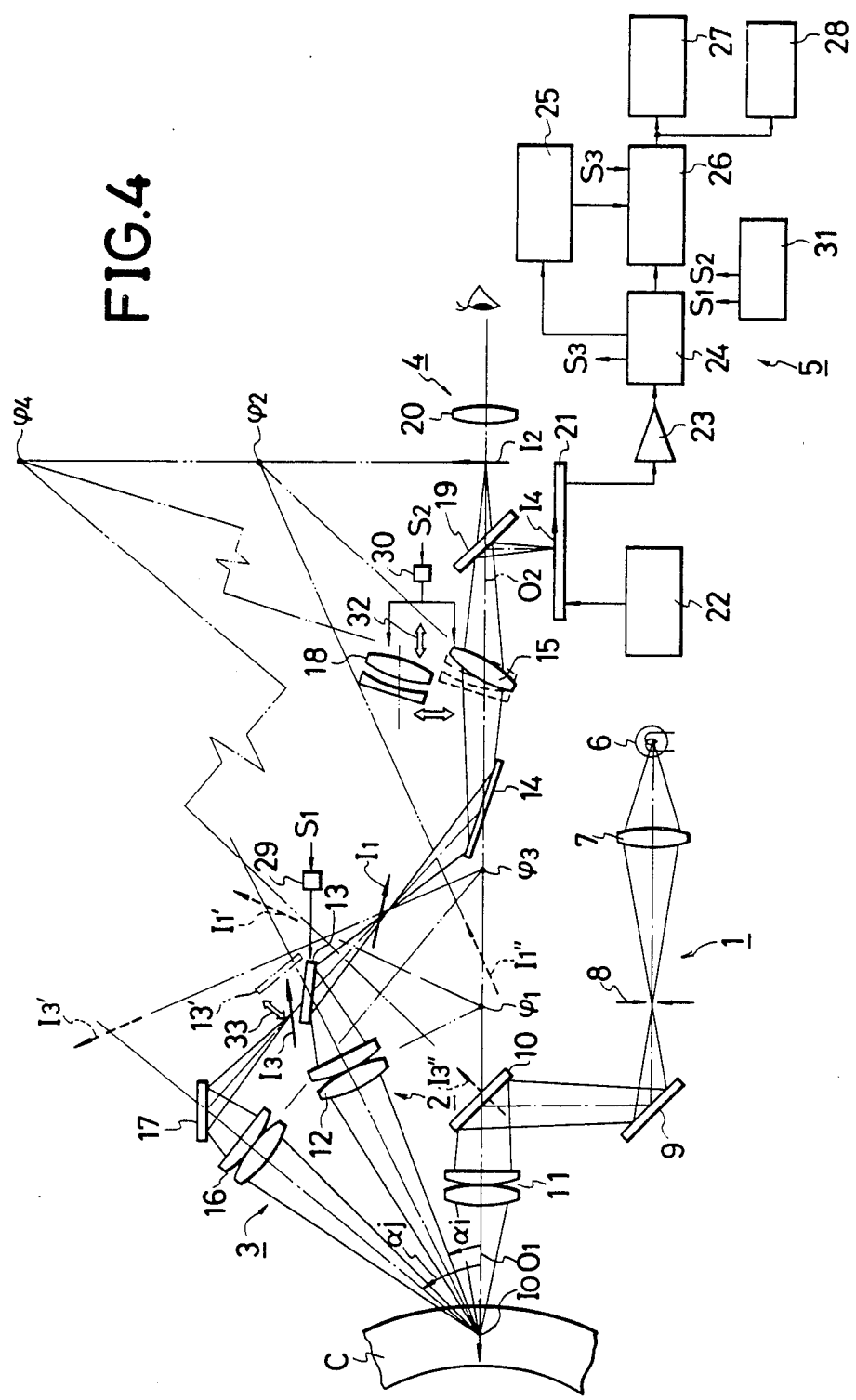
FIG. 4 is a block diagram showing a first embodiment of the apparatus for determining the refective index of the cornea according to this invention.

FIG. 4 shows a first embodiment of an apparatus used for determining the refractive index of the cornea according to this invention.

According to this embodiment, the apparent thicknesses of the cornea to be examined are determined by using the Scheimpflug's principle from the optical image of the cornea sectioned by the slitted light flux, and the refractive index of the cornea is determined therefrom.

The apparatus of this embodiment comprises essentially a illumination system 1 for projecting a slit pattern of illumination light, a first optical measuring system 2, a second optical measuring system 3, an optical system for observation 4 whereby the images from the first and second optical measuring systems are observed in common, and an operation circuitry 5.

The illumination system 1 consists of an illumination light source 6, a condenser lens 7 for condensing the light emitted from the light source 6, slit aperture 8 whereby the slit pattern of illumination light is produced from the light which has passed through the condenser lens 7 by the slit a pair of reflecting mirrors 9 and 10 are provided for reflecting the light beam from the aperture 8 to change its direction, and an image-forming lens 11 is provided so that the light beam from the aperture 8 is focused on the cornea C to form an image.

The first optical measuring system 2 consists of a first object lens 12 having an optical axis making an angle $\alpha_i$ with the optical axis $O_1$ of the illumination system and adapted to form a sectional image $I_0$ of the cornea as a first conjugate image $I_1$, a movable reflecting mirror 13 for converting the direction of the light flux which has passed through said first object lens 12, a reflecting mirror 14 for changing the direction of the light flux from the movable mirror 13 toward a position in the rear of the apparatus, and a first relay lens 15 having a focusing function, said relay lens 15 being selectively brought into the light path. The principal plane of the first object lens 12 is arranged based on the so-called Scheimpflug's principle according to which the incident direction of the slit illumination or the plane of the corneal image $I_0$ intersects at a point $\phi_1$ with the principal plane and the plane of the first imaginary conjugate image of cornea $I_1'$ which will be formed by the object lens 12 when the movable mirror 13 is not in the optical path. The principal plane of the first relay lens 15 is also arranged in accordance with the Scheimpflug's principle so that the plane of the second imaginary conjugate image of cornea $I_1''$ and the plane of the second conjugate image $I_2$ formed by the relay lens 15 meet with the principle plane at one point $\phi_2$.

The second optical measuring system 3 consists of a second object lens 16 having an optical axis making an angle $\alpha_j$ with the optical axis $O_1$ of the illumination light, a reflecting mirror 17 for changing the direction of the light flux from said object lens 16 so that the light flux runs in the same direction as the light flux which has emerged from the first object lens 12 and has been reflected by the movable mirror 13. The reflecting mirror 14 mentioned above and a second relay lens 18 designed to perform a focusing function also constitute a part of the second system 3 and the relay lens 18 is so disposed that it can be selectively brought into the light path. As in the case of the above-described first optical system 2, the principal plane of the second object lens 16 is arranged in accordance with the Scheimpflug's principle so that the plane of the sectional image of cornea $I_0$ and the plane of the imaginary image $I_3'$ of the third conjugate image $I_3$ formed by the second object lens meet with the principal plane at one point $\phi_3$. Likewise, the arrangement of the principal plane of the second relay lens is based on the Scheimpflug's principle such that the plane of the second imaginary image $I_3''$ of the third conjugate image $I_3$ and the plane of the second conjugate image $I_2$ meet with the principal plane at one point $\phi_4$.

The optical system for observation 4 consists of a half-mirror 19 disposed behind the relay lens 15 or the relay lens 18 for splitting into two the light flux from the relay lens, and an eye lens 20 through which the examiner observes the second conjugate image $I_2$ formed by the relay lens 15 or the relay lens 18.

The operation circuits 5 are adapted to measure the width of the fourth conjugate image of the corneal image $I_0$ formed by the relay lens 15 or the relay lens 18 through reflection by the half-mirror 19, that is, the apparent thickness of the cornea C of the eye examined. In a preferred form of the operation circuits 5, it has a charge coupled device (CCD) 21 as means for detecting the width of the conjugate images and comprises driving means 22 for CCD, an amplifier 23 for amplifying the detection output from CCD, a device 24 for measuring the apparent thickness of the cornea C from the detection output amplified by the amplifier 23, a memory 25 for storing the measured values, an operator 26 for operating the refractive index of the cornea from the measurements by the measuring device 24 or those stored in the memory 25, a display 27 showing the result of the operation by the operator 26, a printer 28 whereby the results of the operation are printed out, an actuator for driving the movable mirror 13, an actuator 30 for switching the first relay lens and second relay lens from one to the other, and a changeover switch unit 31 controlling the instructions from the memory 25.

This embodiment is further described below from its operational aspect.

First, the movable mirror 13 and relay lens 15 are brought into the light path to constitute the first optical measuring system as shown in FIG. 4 and then the slit pattern of light is projected to the cornea C through the illumination system 2. While observing the scattered light images of cornea formed from the illumination light through the first optical measuring system and the observation system, the relay lens 15 is moved in the direction of arrow 32 in the drawing to focus the light beams to form a second conjugate image $I_2$ while observing the same. The fourth conjugate image $I_4$ is also correctly formed on said CCD 21. The thus formed fourth conjugate image $I_4$ is detected by CCD 21 and the width of this fourth conjugate image, that is, the "apparent thickness" of the cornea as seen from an angle $\alpha_i$, is measured by the measuring device 24, and the measured value is once stored in the memory 25. Then the changeover switch 31 is operated to actuate the movable mirror driving actuator 29 by a signal $S_1$ from the switch unit to turn the mirror 13 in the direction of arrow 33 in the drawing to let it take the position of 13'. As a result, the light flux from the second object lens 16, which has been intercepted by the back side of the mirror 13, is now allowed to pass on to reach the mirror 14 while the light from the first object lens, which has been incident on the mirror 14, is inhibited from passing thereto. Also, the relay lens switching actuator 30 is driven by a signal $S_2$ issued simultaneously with the signal $S_1$ upon operation of the switch 31, bringing the relay lens 18 into the light path in place of the relay lens 15 to constitute a second optical measuring system. As a result of the formation of this second optical system, the fourth conjugate image $I_4$ of the image $I_0$ in the second optical system, that is, the image at the angle $\alpha_j$, is formed on CCD 21, and consequently the "apparent thickness" at said angle $\alpha_j$ is measured by the CCD 21, the amplifier 23 and the measuring device 24 in the same way as in the case of the first optical system.

The measuring device 24 outputs the results of measurement to the operation circuit 26 and at the same time issues a measurement termination signal $S_3$. Upon receiving this signal, the operation circuit 26 reads out the "apparent thickness" at the angle $\alpha_i$ banked in the memory 25 by the first optical system and calculates the refractive index of the cornea by operation from the both "apparent thicknesses" according to the formulae (1) to (4) shown before. The result of this calculation is indicated on the display 27 and, if necessary, printed out by the printer 28.

Figure 5:
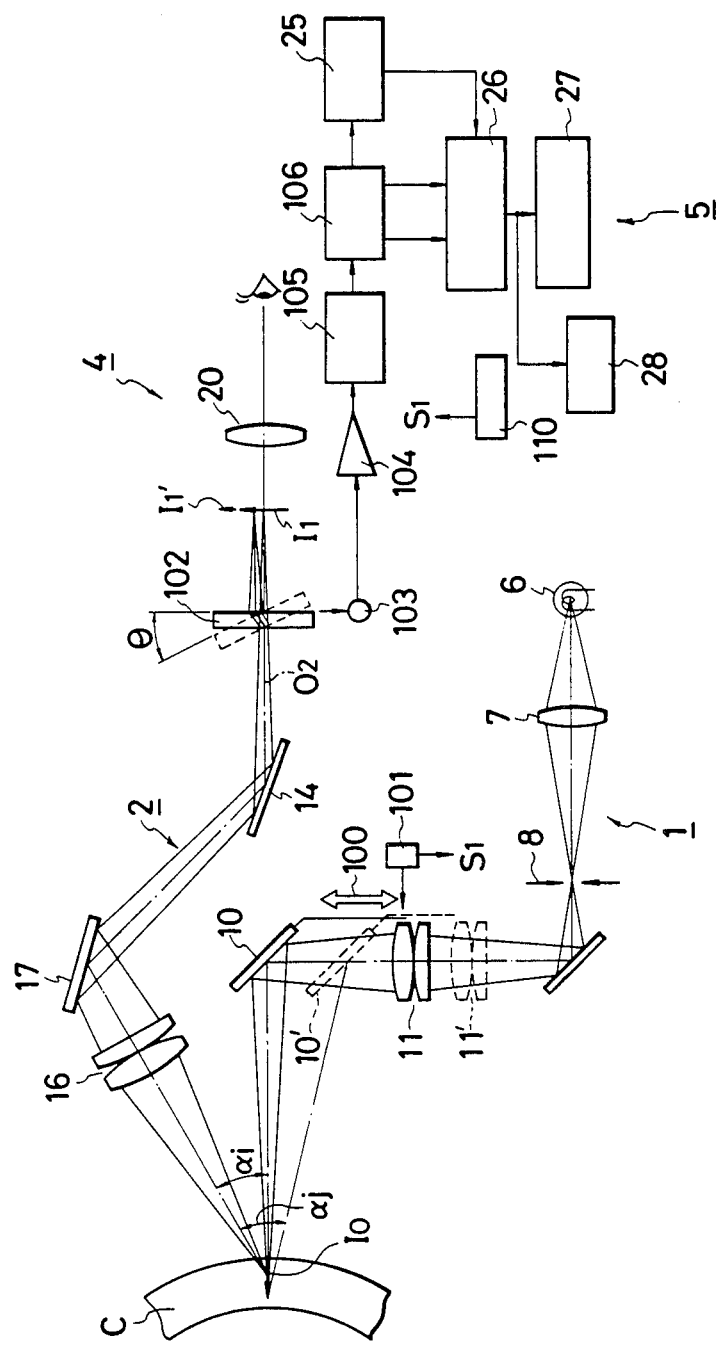
FIG. 5 is a block diagram showing a second embodiment of the apparatus according to this invention.

FIG. 5 shows a second embodiment of an apparatus used for determining the refractive index of the cornea according to this invention. This embodiment features use of a plane-parallel optical element and thus, according to this embodiment, the apparent thickness of the cornea is measured from the angle of turn of the plane parallel element and the refractive index of the cornea is calculated from the result of measurement.

In the previously described first embodiment, the respective optical systems for measuring the sectional image of cornea $I_0$ are arranged to make the angles of $\alpha_i$ and $\alpha_j$, respectively, with the direction of slit pattern projection, but in the instant embodiment, there is adopted a system in which the direction of slit pattern projection is arranged in make the angles of $\alpha_i$ and $\alpha_j$ with the respective optical systems for producing the same effect as in the case of the first embodiment.

This embodiment is described in detail below while referring to FIG. 5. To avoid redundancy of explanation, the component elements which are the same as or equivalent to those in the above-described first embodiment were affixed with the same reference numerals and not given any further explanation.

The illumination system 1 comprises an image-forming lens 11 and a reflecting mirror 10 arranged to be movable integrally with each other in the directions of double-arrow 100 by an actuator 101 driven by the instructions from a switch 110 for projecting the light flux from the slit aperture 8 in two directions at the angles of $\alpha_i$ and $\alpha_j$, respectively, with the optical system 2. Needless to say, the reflecting mirror 10 needs to be turned by an amount necessary for projecting the light flux to the same position as before movement even when the image-forming lens 11 has moved to the position of 11'.

The corneal image $I_0$ is formed as a conjugate image $I_1$ in front of the eye lens 20 of the optical observation system 4 through the object lens 16 and reflecting mirrors 17, 14 of the optical measuring system 2. A plane-parallel optical element 102 is also disposed between the mirror 14 and eye lens 20. This element 102 is arranged so as to be rotatable about an axis vertical to the drawing and also vertical to the optical axis $O_2$ by the operation of an operating handle not shown in the drawing.

The optical element 102 is provided with an angle sensor 103 which senses the angle of turn of the element. The angle sensor 103 is connected to an amplifier 104 so that the detection output from said sensor is amplified by the amplifier 104 and output to an angle counter 105. The angle counter 105 is connected to a calculator 106 which calculates the apparent thickness of the cornea. The calculator 106 is in turn connected to a memory 25, an operation circuit 26, a display 27 and a printer 28 in that order.

Now, the operation of this embodiment is described.

Figure 6:
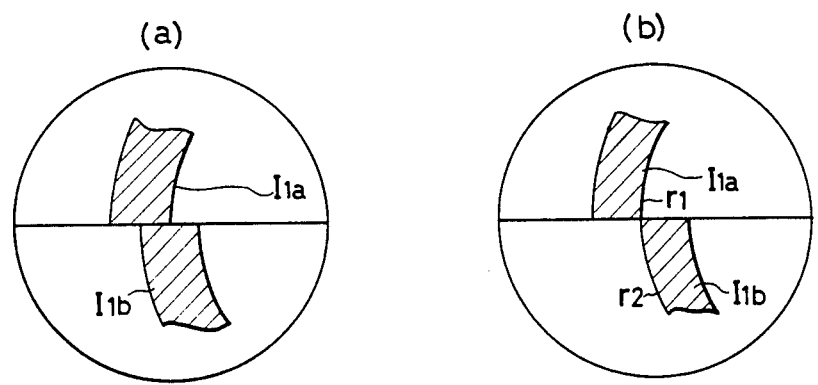
FIG. 6 is a view showing the conditions of an observed image in the second embodiment of the apparatus according to this invention; and, FIG. 7 is a diagrammatic illustration showing the relation between rotation of the plane parallel optical element in said second embodiment of the invention and the cornea to be examined.
Figure 7:
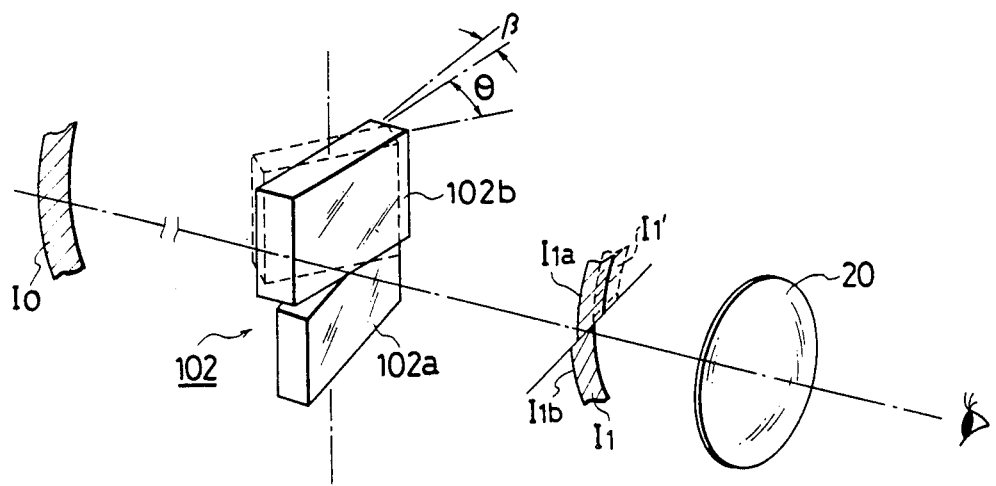

First, the slit pattern of light flux of the illumination system is projected in a direction making an angle $\alpha_i$ with the optical measuring system, and the resultant corneal image $I_0$ is passed through an object lens to form a conjugate image $I_1$. The light flux emerging from the object lens 16 passes through a plane-parallel element 102 such as shown in FIG. 7. This element 102 is divided into a fixed member 102a and a rotatable member 102b as shown in FIG. 7, and they are so arranged that when the rotatable member 102 has turned to a position with an angular distance of $\beta$ from the fixed member 102a, the upper side portion $I_{1a}$ of the conjugate image $I_1$ of the corneal image $I_0$ is observed with a shift laterally from the lower side image portion $I_{1b}$. This condition is illustrated in FIG. 6(a). Then the rotatable member 102b of the planar element is rotated to bring the rear boundary line $r_1$ of the upper image $I_{1a}$ into coincidence with the rear boundary line $r_2$ of the lower image as shown in FIG. 6(b). The amount of rotation $\theta i$ that has been made by the rotatable member 102b is detected by the detector 103 and counted by the angle counter 105, and the determined value is once stored in the memory 25.

Then the switch 110 is operated to drive the actuator 101 to move the lens 11 and mirror 10 to let the light project in a direction of angle $\alpha_j$, which is followed by the same operations as described above, finally counting the amount of turn $\theta_j$ of the rotatable member 102b. The apparent thicknesses $y_i$, $y_j$ of the cornea are determined from the previously obtained value of counting $\theta_i$ and the just obtained one $\theta_j$ according to the previously shown formulae (6) and (7), and the refractive index of the cornea is operationally calculated from said apparent thicknesses $y_i$, $y_j$.

All of these arithmetic operations are performed by the operation circuit 26 and the results thereof are indicated on the display 27 and, if desired, printed out by the printer 28.

The apparatus which may be used according to this invention is not limited in its structural arrangements to the above-described two embodiments. For instance, a pick-up tube may be used instead of CCD as detector in the first embodiment, or a combination of a known photoelectric element and a mechanical or optical scanning mechanism may be used.

Also, instead of providing two optical measuring systems which differ in measuring direction from each other, there may be provided a single optical measuring system arranged movable to perform the same function. Further, the plane-parallel optical element in the second embodiment may be replaced by other suitable image shifting means.

Thus, it is possible according to this invention to determine the refractive index of a cornea in vivo correctly, easily and quickly without extirpating the cornea from a human eye and also without the measuring apparatus contacting the object of determination, and without using an intervening medium.

We claim:
1. A method for determining a refractive index of an object to be measured comprising steps of:
   illuminating the object along an illuminating axis with a slit pattern of light to form an optical section in the object;
   determining a first apparent thickness ($Y_i$) of the object by observing the optical section along a first direction which has an angle $\alpha_i$ with respect to said illuminating axis in a plane which is perpendicular to said optical section and including said illuminating axis;
   determining a second apparent thickness ($Y_j$) of the object by observing the optical section along a second direction which has an angle $\alpha_j$ with respect to said illuminating axis in said plane said angle $\alpha_j$ being different from said angle $\alpha_i$; and
   calculating the refractive index (n) of the object from said first and second apparent thicknesses ($Y_i$, $Y_j$) in accordance with the following formulae:

$$M_i = \sin \alpha_i \left(1 - \frac{Y_i}{r}\right)$$

$$M_j = \sin \alpha_j \left(1 - \frac{Y_j}{r}\right)$$

$$N_i = \alpha_i - \sin^{-1} M_i$$
$$N_j = \alpha_j - \sin^{-1} M_j$$

$$a = \left[\left(\frac{\sin N_i}{M_i}\right)^2 - \left(\frac{\sin N_j}{M_j}\right)^2\right]^2$$

$$b = \sin^2 N_i \sin^2 N_j \left(\frac{1}{M_i^2} + \frac{1}{M_j^2}\right) + \left(\frac{\sin^2 N_i}{M_i^2} + \frac{\sin^2 N_j}{M_j^2}\right)(\cos N_i \cdot \cos N_j - 1)$$

$$c = (\cos N_i - \cos N_j)^2$$

$$N = \sqrt{2\left(\frac{\sqrt{b^2 - ac} - b}{a}\right)}$$

where r is the radius of curvature of the front side of the object to be measured.

2. The method for determining a refractive index according to claim 1, wherein each of said first and second determining steps comprises directly detecting an optical conjugate image of the optical section of the object to determine said apparent thicknesses.

3. The method for determining a refractive index according to claim 1, wherein each of said first and second determining steps comprises dividing an optical conjugate image of the optical section of the object into two parts, shifting one of said parts relative to the other part, and determining said apparent thickness from an amount of the shift of said one part when a rear line of said one part coincides with a front line of said part.

4. A method for determining a refractive index of an object to be measured comprising steps of:
   illuminating the object along a first illuminating axis with a slit pattern of light to form a first optical section in the object;
   determining a first apparent thickness ($Y_i$) of the object by observing the first optical section along a determining axis which has an angle $\alpha_i$ with respect to said first illuminating axis in a plane which is perpendicular to said first optical section and including said first illuminating axis;
   illuminating the object along a second illuminating axis with said slit pattern of the light to form a second optical section at an area where said first optical section is formed in the object, said second illuminating axis having an angle $\alpha_j$ with respect to said determining axis in said plane, said angle $\alpha_j$ being different from said angle $\alpha_i$;
   determining a second apparent thickness ($Y_j$) of the object by observing the second optical section along said determining axis; and
   calculating the refractive index (n) of the object from said first and second apparent thicknesses ($Y_i$, $Y_j$) which are determined by said first and second determining steps in accordance with the following formulae:

$$M_i = \sin \alpha_i \left(1 - \frac{Y_i}{r}\right)$$

$$M_j = \sin \alpha_j \left(1 - \frac{Y_j}{r}\right)$$

$$N_i = \alpha_i - \sin^{-1} M_i$$
$$N_j = \alpha_j - \sin^{-1} M_j$$

$$a = \left[\left(\frac{\sin N_i}{M_i}\right)^2 - \left(\frac{\sin N_j}{M_j}\right)^2\right]^2$$

$$b = \sin^2 N_i \sin^2 N_j \left(\frac{1}{M_i^2} + \frac{1}{M_j^2}\right) + \left(\frac{\sin^2 N_i}{M_i^2} + \frac{\sin^2 N_j}{M_j^2}\right)(\cos N_i \cos N_j - 1)$$

$$c = (\cos N_i - \cos N_j)^2$$

$$N = \sqrt{2\left(\frac{\sqrt{b^2 - ac} - b}{a}\right)}$$

where r is the radius of curvature of the front side of the object to be measured.

* * * * *